United States Patent [19]
Angelo

[11] Patent Number: 5,119,812
[45] Date of Patent: Jun. 9, 1992

[54] ICE MASK

[76] Inventor: Donald Angelo, Box 845, Mt. Juliet, Tenn. 37122

[21] Appl. No.: 716,318

[22] Filed: Jun. 17, 1991

Related U.S. Application Data

[63] Continuation-in-part of Ser. No. 446,186, Dec. 4, 1989, abandoned.

[51] Int. Cl.⁵ ............................................. A61F 7/00
[52] U.S. Cl. .................................... 128/380; 128/402
[58] Field of Search ............... 128/379, 380, 402, 403, 128/399; 62/530, 259.3

[56] References Cited

U.S. PATENT DOCUMENTS

| | | | |
|---|---|---|---|
| 1,627,523 | 5/1927 | Morris | 128/402 |
| 2,477,883 | 8/1949 | LeFohn | 128/402 |
| 3,606,890 | 9/1971 | Gilbert | 128/380 |
| 3,889,684 | 6/1975 | Lebold | 128/402 |
| 4,243,041 | 1/1981 | Paul | 128/402 |
| 4,559,047 | 12/1985 | Kapralis | 128/402 |
| 4,753,241 | 6/1988 | Brannigan et al. | 128/380 |

Primary Examiner—Benjamin Layno
Assistant Examiner—Mark S. Graham
Attorney, Agent, or Firm—Robert M. Sperry

[57] ABSTRACT

An improved face treatment mask having a quantity of a thermal storage substance enclosed within outer layers of material for containing the thermal storage material and having means for releasably securing the face treatment mask in a desired position covering a desired portion of the patient's face. The face treatment mask of the present invention is formed with a plurality of sections, each conforming to a particular portion of the patient's face and selectably removable to permit treatment of only desired portions of the patient's face.

9 Claims, 2 Drawing Sheets

ICE MASK

RELATED CASES

This application is a continuation-in-part of my co-pending application, Ser. No. 446,186, filed Dec. 4, 1989 and now abandoned.

BACKGROUND

1. Field of Invention

This invention relates to facial masks and is particularly directed to facial masks for applying thermal treatment to part or all of a patient's face.

2. Prior Art

It is common practice in caring for facial injuries and the like to apply thermal treatment, such as heat or cold, to reduce swelling, relieve pain and for other beneficial purposes. Unfortunately, it is often difficult, if not impossible, to provide means for applying the thermal treatment evenly over the entire surface of the patient's face. Hot water bottles and ice bags have been widely used. However, it is well known that these devices do not conform well to facial contours and are extremely difficult to maintain in a desired position. Furthermore, many of the prior art facial treatment masks require coverage of areas of the face which may not require treatment. This causes substantial unnecessary discomfort to the patient. Numerous devices have been proposed heretofore for solving these problems. Thus, a search in the United States Patent Office has revealed the following:

| U.S. PAT. NO. | INVENTOR | ISSUED |
| --- | --- | --- |
| 4,190,054 | H. G. Brennan | Feb. 26, 1980 |
| 4,614,189 | V. B. MacKenzie | Sep. 30, 1986 |
| 3,291,761 | M. M. Baker | Jan. 27, 1970 |
| 3,868,984 | B. I. Jorgensen | Mar. 4, 1975 |

Each of these references discloses a face treatment mask. However, none of them prior art devices provides secure coverage of the required areas of the patient's face, while being adjustable to avoid coverage of areas of the patient's face which do not require treatment.

BRIEF SUMMARY AND OBJECTS OF INVENTION

These disadvantages of prior art face treatment masks are overcome with the present invention and an improved face treatment mask is provided which provides secure coverage of the required areas of the patients face, while avoiding coverage of areas of the patient's face which do not require treatment.

The advantages of the present invention are preferably attained by providing an improved face treatment mask having a quantity of a thermal storage substance enclosed within outer layers of material for containing the thermal storage material and having means for releasably securing the face treatment mask in a desired position covering a desired portion of the patient's face. The face treatment mask of the present invention is formed with a plurality of sections, each conforming to a particular portion of the patient's face and selectably removable to permit treatment of only desired portions of the patient's face. Furthermore, the mask is provided with a plurality of spaced vertical and horizontal seams which facilitate shaping the mask to conform to the patient's face, even when the mask is frozen and cloth pads are provided to underlie the mask to protect the patient's skin against burning due to heat or cold.

Accordingly, it is an object of the present invention to provide an improved face treatment mask.

Another object of the present invention is to provide an improved mask for providing thermal treatment to a patient's face.

An additional object of the present invention is to provide an improved face treatment mask for providing thermal treatment to desired portions of a patient's face without applying such treatment to unnecessary areas of the patient's face.

A further object of the present invention is to provide an improved face treatment mask which provides secure coverage of the required areas of the patients face, while avoiding coverage of areas of the patient's face which do not require treatment.

Another object of the present invention is to provide an improved face treatment mask formed with a plurality of spaced vertical and horizontal seams to facilitate shaping the mask to fit a patient's face even when the mask is frozen.

A specific object of the present invention is to provide an improved face treatment mask having a quantity of a thermal storage substance enclosed within outer layers of material for containing the thermal storage material and having means for releasably securing the face treatment mask in a desired position covering a desired portion of the patient's face. The face treatment mask of the present invention is formed with a plurality of sections, each conforming to a particular portion of the patient's face and selectably removable to permit treatment of only desired portions of the patient's face. Furthermore, the mask is provided with a plurality of spaced vertical and horizontal seams which facilitate shaping the mask to conform to the patient's face, even when the mask is frozen and cloth pads are provided to underlie the mask to protect the patient's skin against burning due to heat or cold.

These and other objects and features of the present invention will be apparent from the following detailed description, taken with reference to the figures of the accompanying drawing.

DETAILED DESCRIPTION OF THE INVENTION

Figure 1:
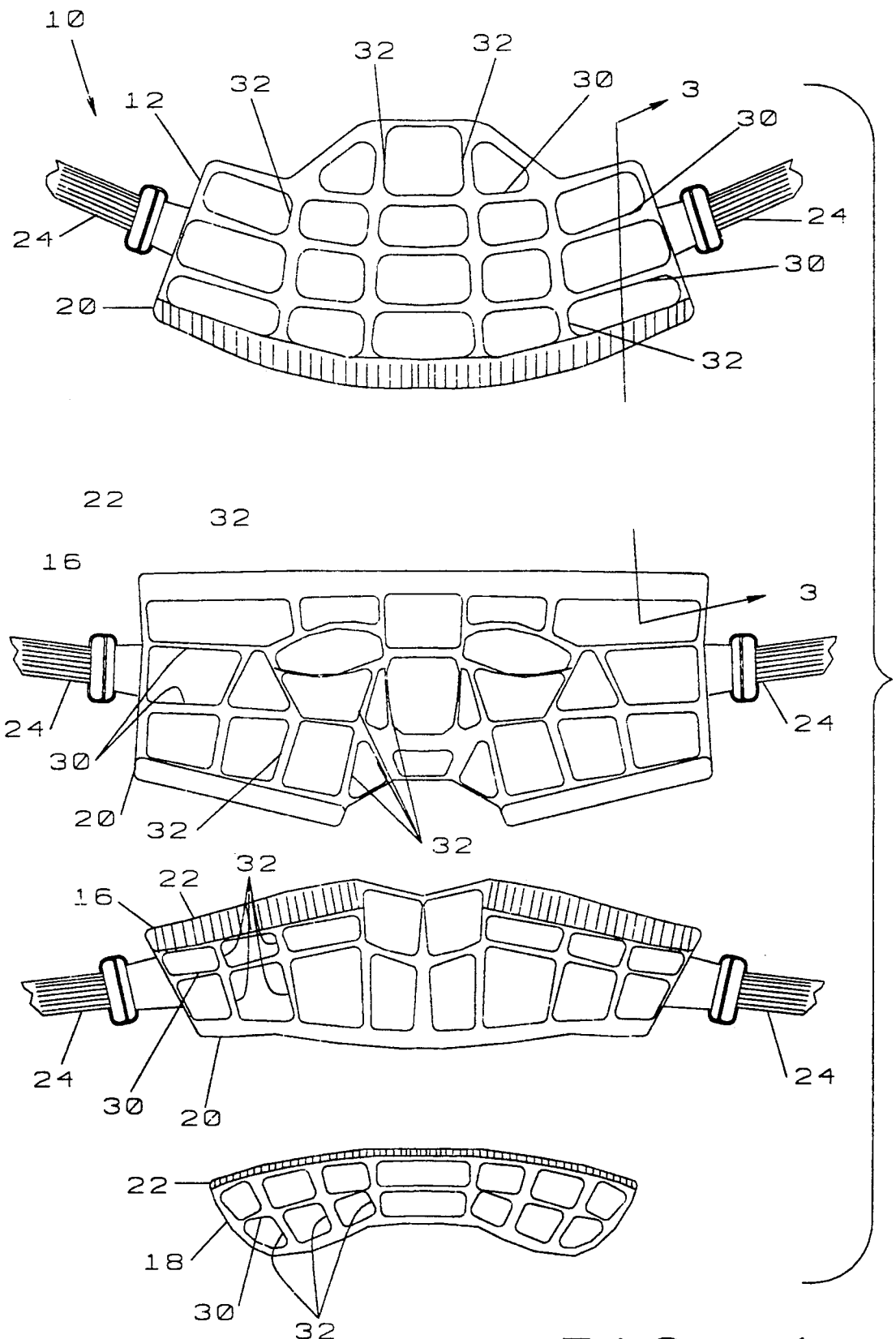
FIG. 1 is a front view of a facial treatment mask embodying the present invention, with the parts of said mask shown separated for clarity.
Figure 2:
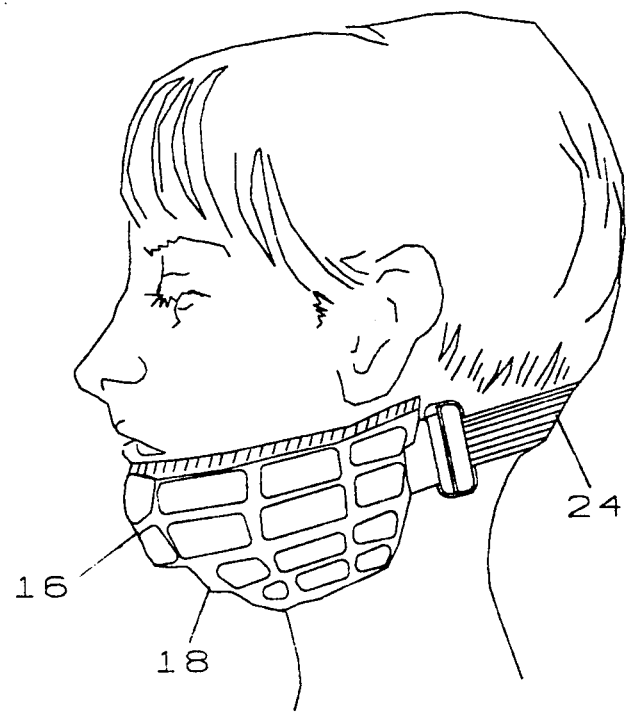
FIG. 2 is a side view showing a patient wearing the jaw portion of the facial treatment mask of FIG. 1.
Figure 3:
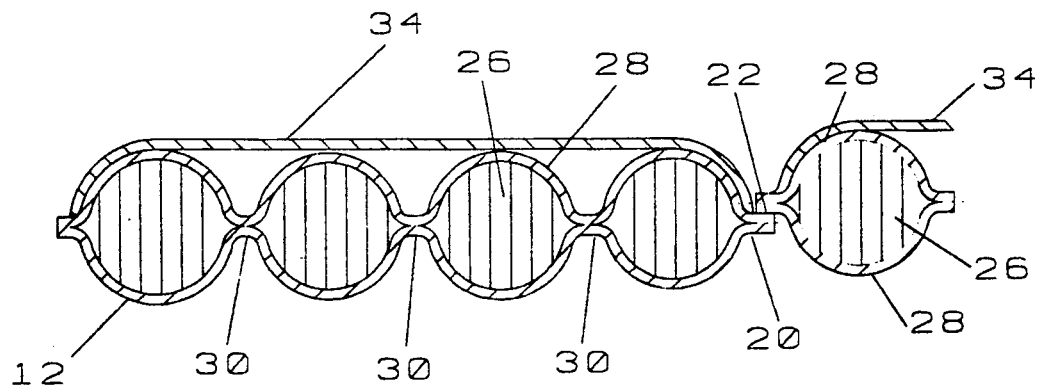
FIG. 3 is a vertical section through the brow member and face member of the facial treatment mask of FIG. 1, taken in the line 3—3 of FIG. 1.

In that form of the present invention chosen for purposes of illustration in the drawing, FIG. 1 shows a facial treatment mask, indicated generally at 10, having a brow member 12, a face member 14 and a jaw member composed of upper jaw member 16 and lower jaw member 18. The members 12, 14, 16 and 18 are preferably formed separate, but each have lower flaps 20 and upper flaps 22 provided along the edges which overlap the corresponding flaps 20 or 22 of the adjacent member or portion of the mask 10 and releasable fastening means, such as strips of hook-and-loop material, are provided on the flaps 20 and 22 to releasably secure the portions 12, 14, 16 and 18 together to form the complete facial treatment mask 10. Alternatively, if desired, the portions 12, 14 and 16 may be formed integral and be provided with perforations along the edges 20 to permit tearing or otherwise separating the portions 12, 14, or 18 for removal. Each of the portions 12, 14 and 16 are provided with suitable means, such as straps 24 for releasably securing the respective portions 12, 14 and 16 of the facial treatment mask 10 in desired positions on the patient. The lower jaw member 18 does not require straps, since it fits under the jaw of the patient, as seen in FIG. 2 and is attached to the upper jaw member 16 by upper flap 22 of the lower jaw member 18 releasably engaging the lower flap 20 of the upper jaw member 16.

Each of the portions 12, 14, 16 and 18 are formed with a quantity of a suitable thermal storage material 26, such as the gelatinous substance commonly used for artificial ice cubes and available commercially under the trade name "Cold Ice" from Cold Ice, Inc., Oakland, Calif. The thermal storage material 26 is enclosed within outer layers 28 formed of a flexible material, such as polyethylene. Also, each of the portions 12, 14, 16 and 18 are formed with a plurality of spaced apart horizontal seams 30 and vertical seams 32. The seams 30 and 32 serve as fold lines to facilitate shaping the mask 10 to conform to the contours of a patient's face even when the mask 10 is frozen. Obviously, the spacing of the seams 30 and 32 may be varied substantially as desired. However, it is preferred that the seams 30 and 32 be spaced apart approximately one-half inch to one inch, since closer spacing tends to restrict the effectiveness of the thermal storage material 26. Finally, if desired, an inner layer or buffer pad 34 may be provided, formed of cloth to protect the patient's skin against burning due to the heat or cold contained in the thermal storage material 26. If desired, the cloth layer or buffer pad 34 may be releasably attached to the inner surfaces of the portions 12, 14, 16 and 18 by suitable means, such as adhesive backing or hook-and-loop material. Alternatively, the inner layer 34 may simply be placed on the patient's skin and will be held in place by the straps 24 and the associated portions 12, 14, 16 and 18.

In use, the facial treatment mask 10 may be heated or chilled, as appropriate, prior to application and, even if frozen, the mask 10 can be shaped to conform to the contours of the patient's face by bending the mask along the bend lines formed by the seams 30 and 32. Once applied, the mask 10 will serve to continually supply heat or cold to the covered areas of the patient's face. However, it frequently occurs that the facial area requiring treatment is less than the total area of the patient's face. With the facial treatment mask 10 of the present invention, it is possible to allow for treatment of lesser areas by removing one or more of the portions 12, 14, 16 or 18, as appropriate. Brow member 12 of the facial treatment mask 10 is formed to cover the patient's forehead from approximately the hairline to just above the patient's eyebrows, while face member 14 is formed to cover the area between the patient's eyebrows and mouth without blocking the patient's view. Upper jaw member 16 is formed to cover the patient's jaw area from just below the mouth to just below the jawbone, while lower jaw member 18 is formed to cover the under portion of the patient's jaw, as best seen in FIG. 2. As indicated above, each of the portions 12, 14, 16 and 18 is separable. Thus, if the patient has a bruised forehead, portions 14, 16 and 18 could be removed and only portion 12 would be applied. This would assure that appropriate thermal treatment was applied to the injured area, but would not require causing discomfort to the rest of the patient's face. Similarly, if the patient has had a cheek injury, only portion 14 need be employed; while portions 12, 16 and 18 can be removed to prevent causing discomfort to the patient's forehead and lower jaw areas. Again, if the patient has injuries on their forehead and lower jaw, portions 12 and 16 may be applied, while portion 14 is removed. If the injury is to the upper portion of the patient's jaw, lower jaw member 18 could also be removed, if desired. Thus, thermal treatment is applied only to the injured areas and is not applied to cause unnecessary discomfort to uninjured areas. Also, it will be apparent that, by suitable adjustment of the straps 24 and bending along the seams 30 and 32, the facial treatment mask 10 may be applied over swollen or bandaged areas without causing unnecessary discomfort.

Figure 4:
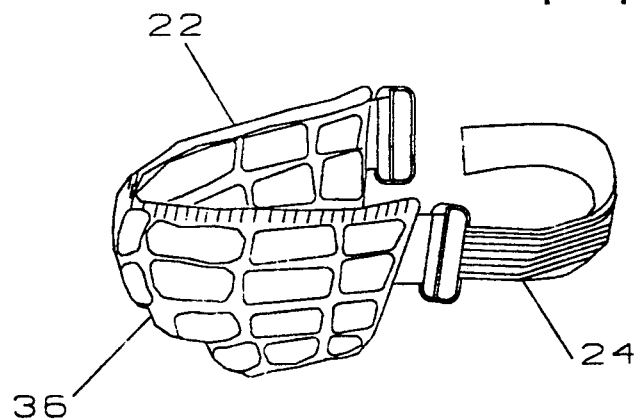
FIG. 4 is a side view of an alternative form of the jaw portion of the facial treatment mask of FIG. 1.

If desired, the upper jaw member 16 and lower jaw member 18 maybe joined together to form a single member, as seen at 36 in FIG. 4. Unitary jaw member 36 serves the same function as the separate upper jaw member 16 and lower jaw member 18, described above, but may be preferred when it is necessary to treat the entire jaw area, instead of just a portion of this area.

Obviously, numerous variations and modifications can be made without departing from the spirit of the present invention. Therefore, it should be clearly understood that the forms of the present invention described above and shown in the figures of the accompanying drawing are illustrative only and are not intended to limit the scope of the present invention.

What is claimed is:

1. A thermal treatment face mask comprising:
    said mask being formed with a plurality of releaseably fastened members each formed of a plurality of layers of flexible material and containing a quantity of a thermal storage material sandwiched between said layers and having means for releasably securing the face treatment mask in a desired position covering a desired portion of the patient's face;
    a first of said members for covering the region from approximately the hairline of the patient to just above the patient's eyebrows and having a plurality of seams extending vertically and horizontally to divide said first of said members into a plurality of generally rectangular seqments to enhance the flexibility of said first of said members in conforming to the shape of the patient's face,
    a second of said members for covering the region from just above the patient's eyebrows to the upper edge of the patient's mouth without blocking the patient's vision and formed with a plurality of seams extending generally vertically and horizontally to divide said second of said members into a plurality of seqments to enhance the flexibility of said first of said members in conforming to the shape of the patient's face, and
    at least one other member for covering the patient's jaw and having a plurality of seams extending vertically and horizontally to divide said other of said members into a plurality of generally rectangular seqments to enhance the flexibility of said other of said members in conforming to the shape of the patient's jaw.

2. The thermal treatment mask of claim 1 wherein:
said at least one of said members comprises an upper jaw member for covering the patient's jaw area from just below the mouth to just below the jawbone.

3. The thermal treatment mask of claim 1 wherein:
said at least one other member comprises a lower jaw member for covering the under portion of the patient's jaw and having a plurality of seams extending vertically and horizontally to divide said lower jaw into a plurality of generally rectangular segments to enhance the flexibility of said lower jaw in conforming to the shape of the patient's lower jaw.

4. The thermal treatment mask of claim 1 further comprising:
flaps provided along adjacent edges of each of said members having means on said flaps for releasably attaching each of said members to an adjacent one of said members.

5. The thermal treatment mask of claim 4 wherein:
said means for releasably attaching is hook-and-loop material.

6. The treatment mask of claim 1 further comprising:
a layer of cloth covering an inner surface of said mask to protect the patient's face against burning due to the heat or cold contained within said thermal storage material.

7. The treatment mask of claim 6 wherein:
said cloth layer is releasably attached to an inner surface of said flexible material.

8. The treatment mask of claim 6 wherein:
said cloth layer is provided with an adhesive backing for releasable attachment to said flexible material.

9. The treatment mask of claim 6 wherein:
said cloth layer is provided with hook-and-loop material for releasable attachment to said flexile material.

* * * * *